United States Patent [19]

Schvester et al.

[11] Patent Number: 5,203,138
[45] Date of Patent: Apr. 20, 1993

[54] METHOD FOR PRESERVING FRESH CUT FLOWERS OR PLANT CUTTINGS

[75] Inventors: Pascal Schvester; Nathalie Savich, both of Chicago, Ill.

[73] Assignee: American Air Liquide, Inc., Countryside, Ill.

[21] Appl. No.: 632,091

[22] Filed: Dec. 12, 1990

[51] Int. Cl.$^5$ .................. B65B 55/00; B65B 31/02
[52] U.S. Cl. ........................ 53/428; 53/434; 47/58; 47/DIG. 11
[58] Field of Search ............. 53/432, 434, 440, 472, 53/428; 47/58, DIG. 9, DIG. 11

[56] References Cited

U.S. PATENT DOCUMENTS

| | | | |
|---|---|---|---|
| 2,302,639 | 11/1942 | Moore | 53/440 X |
| 3,183,057 | 5/1965 | Marks et al. | 53/432 X |
| 3,584,428 | 6/1971 | Falk | 53/434 |
| 3,715,860 | 2/1973 | Esty | 53/434 |
| 4,055,931 | 11/1977 | Myers | 53/432 X |
| 4,411,918 | 10/1983 | Cimino et al. | 53/432 X |
| 4,970,844 | 11/1990 | Domenichiello | 53/434 X |

FOREIGN PATENT DOCUMENTS 1431047  4/1976  United Kingdom ............... 53/432

Primary Examiner—Horace M. Culver
Attorney, Agent, or Firm—Oblon, Spivak, McClelland, Maier & Neustadt

[57] ABSTRACT

A method for preserving fresh cut flowers or plant cuttings, which entails:

a) subjecting said fresh cut flowers or plant cuttings to a gas mixture containing about 80% to about 98% $N_2O$, about 2% to about 20% $O_2$, with the remainder being $N_2$ under refrigeration, and b) subjecting said fresh cut flowers or plant cuttings to a gas mixture containing about 50 to about 80% $N_2O$, and a minimum of about 20% $O_2$, with the remainder being $N_2$; or subjecting said fresh cut flowers or plant cuttings to air at a temperature in the range of about 0° C. to temperature.

19 Claims, 1 Drawing Sheet

```
┌─────────────────────────────────┐
│ SUBJECT FRESH CUT FLOWERS OR    │
│ PLANT CUTTINGS TO A FIRST GAS   │
│ MIXTURE CONTAINING ABOUT 80% TO │
│ 90% N2O, AND ABOUT 2% TO 20%    │
│ O2, THE REMAINDER BEING N2,     │
│ UNDER REFRIGERATION             │
└─────────────────────────────────┘
                 │
                 ▼
┌─────────────────────────────────┐
│ SUBJECT THE FRESH CUT FLOWERS OR│
│ PLANT CUTTINGS TO A SECOND GAS  │
│ MIXTURE CONTAINING ABOUT 50% TO 80%│
│ N2O, AND A MINIMUM OF 20% O2, WHICH│
│ IS GREATER THAN THE AMOUNT OF O2 IN│
│ THE FIRST GAS MIXTURE, THE REMAINDER│
│ BEING N2, AT A TEMPERATURE OF ABOUT │
│ 0°C TO 8°C; OR SUBJECT THE FRESH CUT│
│ FLOWERS OR PLANT CUTTINGS TO AIR AT │
│ A TEMPERATURE IN THE RANGE OF ABOUT │
│ 0°C TO AMBIENT TEMPERATURE          │
└─────────────────────────────────┘
```

METHOD FOR PRESERVING FRESH CUT FLOWERS OR PLANT CUTTINGS

BACKGROUND OF THE INVENTION

1. Field of Use

The present invention relates to a method for preserving fresh cut flowers or plant cuttings.

2. Description of the Background

It has been known for a number of years that horticultural products, including flowers, fruit and vegetables in a controlled atmosphere, are sensitive to the temperature, concentration of carbon dioxide and oxygen gases and humidity in spaces where these materials are stored. Hence, conventional methods for preserving horticultural products have involved the regulation of these factors. For example, British patent 1,255,700 describes a method of preserving horticultural products wherein the products are stored in an enclosed space containing an artificial atmosphere which is contained inside a cold chamber to effect indirect refrigeration of the products. The method of this patent also entails the circulation of an artificial atmosphere within the contained space, the composition, humidity and temperature of which is controlled externally.

Although some success has been attained with this method, in general, the use of refrigeration for the preservation of horticultural products either in transportation or in storage is quite expensive, and, thus, undesirable.

More recently, gas packaging has been used to extend the shelf-life of fresh food products. While gas packaging techniques have been used in an attempt to extend the shelf-life of other products such as cut flowers or plant cuttings, it is found that the results obtained thereby are inadequate.

In gas packaging, gases such as carbon dioxide or sulfur dioxide are used in the effort to preserve fresh cut flowers or plant cuttings. Unfortunately, the tolerance of flowers or plant cuttings to elevated partial pressures of these gases is quite low.

It is known that by lowering the concentration of oxygen, a longer survival of plant material can be effected due to the reduction in respiration rate. Hence, by exposing fresh cut flowers or plant cuttings to carbon dioxide or sulfur dioxide a minor shelf-life extension is obtained in some cases, however, in most cases, little preservation effect is obtained as the vegetal deterioration is initiated and activated by the production and release of ethylene in the plant tissues.

When fresh cut flowers or plant cuttings are exposed to ethylene, initially the vegetal material changes color by yellowing of the leaves or petals. Thereafter, the vegetal material acquires a burned appearance, whereinafter ultimate necrosis of the vegetal material occurs. At present, no gas or gas mixture or gas technique has demonstrated an ability to reduce or control the production of ethylene and its effects on plant material. Hence, producers of fresh cut flowers or plant cuttings have relied primarily on temperature control or ethylene scavengers to avoid the build-up of ethylene within packages containing the plant material. Although it is possible to decrease the production rate of ethylene by decreasing the temperature, ethylene production by the vegetal material is not entirely suppressed. Moreover, when the plant material is subjected to an unexpected increase in temperature, ethylene production rapidly resumes and irreversible damage to the appearance of the plant material is observed.

Although chemical scavengers are effective in absorbing ethylene released by plants in their packages, such scavengers do not have any effect on biochemical ethylene production at the cellular level. Hence, ethylene scavengers are only useful to limit the reabsorption of ethylene by the non-ethylene producing portion of the vegetal material.

Hence, a need continues to exist for a means by which the biochemical production of ethylene, itself, may be decreased, in order to improve the shelf-life and color of fresh cut flowers or plant cuttings.

SUMMARY OF THE INVENTION

Accordingly, it is an object of the present invention to provide a method for the preservation of fresh cut flowers or plant cuttings, whereby the biochemical production of ethylene is decreased.

It is also an object of the present invention to provide a particular gas mixture which may be used to preserve fresh cut flowers or plant cuttings, by decreasing the biochemical production of ethylene.

These objects and others which will be described hereinbelow, are provided by a process for preserving fresh cut flowers or plant cuttings, which entails:

a) subjecting fresh cut flowers or plant cuttings to a gas mixture containing $N_2O$ in a minimum concentration of about 80% and a maximum concentration of about 98%, and $O_2$ in a minimum concentration of about 2% and a maximum concentration of about 20%, with the remainder being $N_2$, under refrigeration; and then b) subjecting said fresh cut flowers or plant cuttings to an atmosphere containing a gas mixture having a minimum of about 20% $O_2$, about 50 to 80% $N_2O$, with the remainder being $N_2$ at a temperature in the range of about 0° to 8° C.; or to air at a temperature of from 0° C. to ambient temperature.

DETAILED DESCRIPTION OF THE PREFERRED EMBODIMENTS

Figure 1:
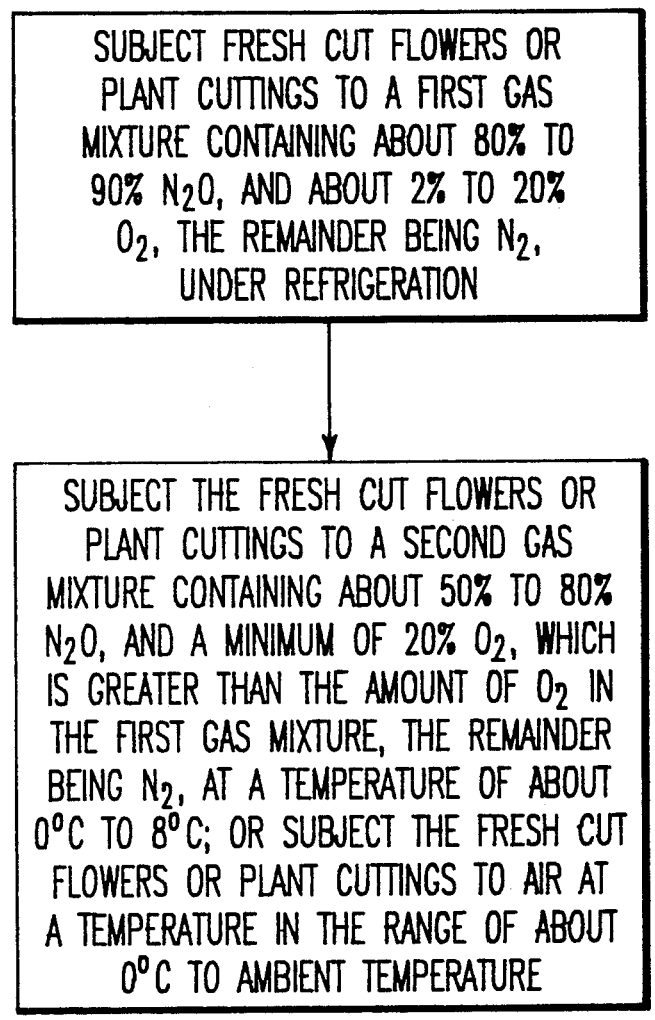
FIG. 1 illustrates the steps in one process embodiment of the present invention.

In accordance with the present invention, a method is provided for the preservation of fresh cut flowers or plant cuttings, thereby improving the shelf-life and the color of fresh cut flowers or plant cuttings.

The present invention provides a multistep approach utilizing a first phase which entails introducing a gas mixture containing $N_2O$ in a minimum concentration of about 80% and a maximum concentration of about 98%. Also present are $O_2$ in a minimum concentration of about 2% and a maximum concentration of about 20%, the remainder being $N_2$. The plant material is maintained in the presence of this atmosphere under refrigeration for a maximum of about 24 hours.

By "refrigeration" is generally meant below ambient temperature or less than about 10° C. It is preferred, however, that this temperature be less than 8° C. It is most preferred that this temperature be in the range of about 0° C. to about 5° C.

Thereafter, the fresh cut flowers or plant cuttings are subjected to an atmosphere containing a gas mixture having a minimum of about 20% $O_2$, and about 50 to 80% $N_2O$, with the remainder being $N_2$ at a temperature in the range of about 0° C. to about 8° C.

Alternatively, as a second step, the fresh cut flowers or plant cuttings may be subjected to air at a temperature of about 0° C. to up to ambient temperature. In accordance with this option, it is preferred that the ambient air not be above a temperature of about 20° C.

In accordance with the present invention, the above-recited second step conditions are maintained for the entire residual shelf-life of the plant material. Quite surprisingly, it has been discovered that this multistep procedure decreases or ceases the biochemical production of ethylene during the first step of the process. Although this effect remains for a limited period of time, it is sufficiently long enough to allow, in the second step, the reintroduction of $O_2$ in partial pressures equivalent to that of air. Thus, a normal respiration rate of the plant material is reinstated for the remainder of the product shelf-life without massive accumulations of ethylene.

To be used in accordance with the present method are the following specific gas mixtures. In the first step, a gas mixture is used containing $N_2O$ in a minimum concentration of about 80% and a maximum concentration of about 98%. The complementing gases are $O_2$, which is present in a minimum concentration of about 2%, and a maximum concentration of about 20%, with the remainder being $N_2$. Thereafter, in the second step, a gas atmosphere containing a mixture having a minimum of about 20% of $O_2$, and about 50 to about 80% of $N_2O$, with the remainder being $N_2$ is used at a temperature of about 0° to 8° C. Alternatively, in the second step, as noted above, air may be used at a temperature of about 0° C. to ambient temperature.

The present invention is distinctive and advantageous as a multistep process in which the parameters of each stage are well defined according to gas compositions and process parameters. Second, and quite surprisingly, in accordance with the present invention it has been discovered that $N_2O$ slows down or ceases the biochemical production of ethylene by plant material. Third, the contact of an elevated partial pressure of $N_2O$ with the vegetal material is limited in time and applies to only the first step of the process. Fourth, a minimum of about 20% $O_2$ must be applied to the packaged material during the second phase of the process so the product shelf-life limit is obtained.

The present process and gas mixtures may be used as a gas packaging technique or may also be used in conjunction with conventional controlled environment storage apparati. Also, any conventional oxygen permeable or oxygen impermeable bags may be used in gas packaging the vegetal material in accordance with the present invention.

In accordance with the present invention, the term "oxygen permeable" is generally meant to refer to materials, such as films or bags, for example, which have permeabilities to oxygen of about 75 to 200 $cm^3/m^2/day$ at 4° C. The term "oxygen impermeable" is generally meant to refer to such materials having permeabilities to oxygen of only about 5 to 10 $cm^3/m^2/day$ at 4° C.

Membranes satisfying the above requirements are well known to those skilled in the art. For example, see *The Polymer Handbook*, by J. Brandrup and E. H. Immerguf, Wiley (Third Edition, 1989), in particular, pp. 435–449 on "Permeability and Diffusion Data".

In the present specification, the term "barrier membrane", "barrier film" or "barrier bag" refers to an oxygen impermeable membrane, film or bag, respectively, as defined above.

FIG. 1 illustrates the steps of one process embodiment of the present invention in a block diagram. The first block at the top of the page illustrates step a), and the block beneath the same illustrates step b).

The present invention will now be further described by reference to certain examples which are provided solely for purposes of illustration and are not intended to be limitative.

EXAMPLE 1

15 cm long geranium cuttings are separated from the parent plant. Bags made of an oxygen barrier film containing 20 fresh cuttings are flushed with a modified atmosphere. Some bags are vacuum flushed.

Another batch of cuttings is placed in perforated bags.

Another batch of cuttings is placed in perforated bags along with an ethylene scavenger.

All bags are then subjected to the same time/temperature process. Bags containing a modified atmosphere are punched several times with a needle at the end of the first phase and then exposed to second phase temperature. Vacuum bags are never perforated.

The results obtained are summarized in the following table:

| bag | treatment | |
|---|---|---|
| | $24^h$ at 4° C., perforation of the bag then $72^h$ at 25° C. | 24 h at 4° C., perforation of the bag then $72^h$ at 4° C |
| 80% $N_2O$/20% $O_2$ in $O_2$ barrier bags | very little chlorosis deep green leafs | no chlorosis or necrosis deep green leafs |
| vacuum in $O_2$ barrier bags | dead prior sticking | dead prior sticking |
| perforated bags | ¼ dead and chlorosis pale to medium green leafs | ¼ necrosis pale to medium green leafs |
| ethylene scavenger in perforated bags | ¼ necrosis, little chlorosis medium green leafs | little chlorosis or necrosis medium green leafs |

EXAMPLE 2

Geranium cuttings are subjected to an identical test procedure except that the $O_2$ barrier film is replaced by a $O_2$ permeable barrier film for the modified atmosphere packaged samples. The $O_2$ permeation rate of the film material is 16,000 $cc/m^2$ per 24 hours.

No bag perforation is performed after the first 24 hours of treatment in the case of the modified atmosphere packaged cuttings.

The results obtained are summarized below:

| bag | treatment | |
|---|---|---|
| | $24^h$ at 4° C. then $72^h$ at 25° C. | 120 hours at 4° C. |
| 98% $N_2O$/2% $O_2$ | Little or no burn medium to deep green leafs | no chlorosis or necrosis deep green leafs |
| perforated bags | ¼ dead and chlorosis pale to medium green leafs | ¼ dead pale-green leafs |
| ethylene scavengers in perforated bags | ¼ necrosis, little chlorosis pale to medium green leafs | ¼ necrosis pale to medium green leafs |

EXAMPLE 3

25 cm long cut red or yellow roses are plunged into water which is maintained at a temperature of between 37° and 43° C. The water is acidified to a pH of 3.5 with citric acid. The roses are maintained in these conditions for between 12 and 24 hours. The roses are then packaged in groups of 5 in an $O_2$ barrier bag containing a mixture of 80% $N_2O$ and 20% $O_2$. A control is packaged under air. The temperature is maintained at 34° F. throughout the test. After 3½ weeks, bags are punctured with 4 needle size holes.

The results obtained are described in the following Table.

|  | Yellow | Red | Yellow | Red | Yellow | Red | Yellow | Red |
|---|---|---|---|---|---|---|---|---|
| Time Weeks | 1 | 1 | 2 | 2 | 3 | 3 | 5 | 5 |
| Treatment |  |  |  |  |  |  |  |  |
| Air | Good Aspect | Good Aspect | Browning Leaf Discoloration | Browning Leaf Discoloration | Severe Browning Unsalable | Severe Browning Unsalable | Dead | Dead |
| $N_2O/O_2$ 80%/20% | Good | Good | Good | Good | Good | Good Some Petal Drop | Good | Good More Petal Drop |

After 5 weeks, flowers are removed from packages and plunged into warm citric acidified water for 12 h. Another 7 days of post storage shelf life is obtained at room temperature.

In the case of respiring flowers, for example roses, it is known that elevated partial pressures of $CO_2$ can have a considerable effect upon the respiration rate of the flowers. For example, a low partial pressure of $CO_2$, such as 5% in combination with refrigerated conditions, can decrease the respiration rate of these flowers by a factor of 2 to 3. However, at higher $CO_2$ concentration, $CO_2$ becomes an adverse factor in the preservation process.

At concentrations above 10 to 15%, flowers are injured and such symptoms of $CO_2$ injury as browning of petal edges, changed in flower color, discoloration of petal veins and failure of buds to open are observed. Unfortunately, storage temperatures of about 32° F. range accentuate the injurious effect of $CO_2$. However, the present invention also provides a process by which these problems can be prevented.

In general, fresh cut flowers are placed in a bunch in a pouch made of barrier material and flushed with a gas mixture which is about 80% $N_2O$/20% $O_2$. Then, small packages containing a small amount of lime, generally not more than about 50 g., are placed in pouches containing the flower. These packages are made with a $CO_2$ permeable film material having a $CO_2$ permeability determined so that the $CO_2$ produced from the respiration of the flowers will be in part absorbed by the lime.

It is more preferred that about 10 grams of lime per flower is used per package. It is even more preferred, however, if between about 2 and 5 grams of lime per flower is used per package.

By the above term "$CO_2$ permeable" film material is meant a film material having a permeability to $CO_2$ which is about 75 to 200 cm$^3$/m$^2$/day at 4° C. By contrast, the term "$CO_2$ impermeable" film material would mean a permeability to $CO_2$ which is only about 5 to 10 cm$^3$/m$^2$/day at 4° C.

Further, as noted above, packages containing the cut flowers and lime bags are then placed in a refrigerated storage room. Generally, a temperature of between about 32° and 36° F. may be used. However, it is preferred to use a temperature of about 32° F.

Packages containing the cut flowers and lime bags are then placed in a refrigerated storage room.

As the cut flowers respire, $O_2$ is gradually depleted and $CO_2$ is produced. $N_2O$ protects the flowers against bacteriological and fungal development. The $CO_2$ produced permeates through the lime pouch and is absorbed by the lime. As the permeation rate of $CO_2$ is less than the production rate, $CO_2$ begins to accumulate in the package. This accumulation leads to a decrease in respiration rate for the flower and, thus, to a decrease in $CO_2$ production.

By selecting the proper parameters, equilibrium between the $CO_2$ production rate and the $CO_2$/permeation-absorption rate by the lime is reached. An artificially $CO_2$ controlled atmosphere is, therefore, generated whereby a concentration of 5% of $CO_2$ can be maintained throughout the shelf-life of the flowers.

After about one month in storage, the cut flowers are removed from the packages. Stems are cut and placed in a citric acid solution having a pH of about 3.5 at a slightly elevated temperature overnight.

By using the above-described procedure, an additional 7 days or so of shelf-life may be obtained. The above procedure will now be illustrated by an example which is provided solely for illustration and is not intended to be limitative.

EXAMPLE 4

Fresh cut roses are placed in bunches of 10 or more flowers in a pouch made of barrier material and flushed with a 80% $N_2O$/20% $O_2$ gas mixture.

Small packages containing between about 10 and 50 g. of lime are placed in pouches containing the roses. The packages are made with a $CO_2$ permeable film material having a $CO_2$ permeable determined so that the $CO_2$ produced from the respiration of the roses is, in part, absorbed by the lime.

The packages containing the roses and lime bags are then placed in a refrigerated storage room.

After 40 days of storage, the roses are taken out of the packages. Stems are cut and placed in a 40° C. aqueous citric acid solution of pH 3.5 overnight. Seven days of additional shelf-life are thereby obtained.

Although the refrigerated storage period utilized in the above Example is 40 days, storage periods of as little as one day may be used. Generally, however, refrigerated storage periods of longer than one day are used. For example, a refrigerated storage period of several days, one week, two weeks, three weeks or one month may be used. If desired, refrigerated storage periods of longer than one month may be used.

The procedure described above, immediately preceding Example 4, is effective for any type of respiring flowers. The previously described procedure is effective for geranium cuttings. It appears that the first described procedure is better for geranium cuttings due to the enhanced production of ethylene by geraniums. Thus, the first described procedure may be most advantageously used with flowers which are high producers of ethylene.

The processes of the present invention may be advantageously practiced by generating a continuous gas flow of the appropriate gas mixture constituent concentrations through a gastight container or using an oxygen permeable container material.

Having described the present invention, it will now be apparent to one of ordinary skill in the art that many changes and modifications can be made to the above-described embodiments without departing from the spirit and the scope of the present invention.

What is claimed as new and desired to be secured by Letters Patent of the United States is:

1. A process for preserving fresh cut flowers or plant cuttings, which comprises:
   a) subjecting said fresh cut flowers or plant cuttings to a first gas mixture comprising about 80 to 98% $N_2O$, and about 2 to 20% $O_2$, with the remainder being $N_2$, under refrigeration, and
   b) subjecting said fresh cut flowers or plant cuttings to a second gas mixture comprising about 50 to 80% $N_2O$, and a minimum of 20% $O_2$, which amount of $O_2$ is greater than the amount of $O_2$ in said first gas mixture, with the remainder being $N_2$, at a temperature in the range of about 0° to 8° C.

2. The process of claim 1, wherein said refrigeration comprises a temperature of about 0° C. to 5° C.

3. The process of claim 1, which further comprises providing a continuous flow of the required gaseous mixtures through an opening in a gas tight container.

4. The process of claim 3, which further comprises adding lime to said gas tight container container in an amount effective for absorbing at least a portion of $CO_2$ produced by said flowers or plant cuttings.

5. The process of claim 1, which further comprises providing a flow of the required gaseous mixtures through an oxygen permeable material of an oxygen permeable container.

6. The process of claim 5, which further comprises adding lime to said oxygen permeable container in an amount effective for absorbing at least a portion of $CO_2$ produced by said flowers or plant cuttings.

7. A process for preserving fresh cut flowers or plant cuttings, which comprises:
   a) placing said fresh cut flowers or plant cuttings in a pouch made of a barrier material and flushing the pouch with a gas mixture which is 80% $N_2O$ and 20% $O_2$,
   b) placing a package containing an amount of lime, effective for absorbing at least a portion of $CO_2$ produced by said cut flowers or plant cuttings, in said pouch containing, said cut flowers or plant cuttings, said package being made with $CO_2$ permeability such that the $CO_2$ produced from the respiration of the cut flowers or plant cuttings will be, at least in part, absorbed by said lime, and
   c) placing said pouch containing said cut flowers or plant cuttings and lime package in a refrigerated storage room, and storing said pouch in said storage room.

8. The process of claim 7, wherein in step b), less than 10 grams of lime per flower is used per package.

9. The process of claim 7, wherein said fresh cut flowers or plant cuttings are fresh cut roses.

10. The process of claim 7, wherein said fresh cut flower or plant cuttings are maintained in refrigerated storage for at least about one day.

11. The process of claim 8, wherein about 2 to 5 grams of lime per flower is used per package.

12. A process for preserving fresh cut flowers or plant cuttings, which comprises:
   a) subjecting said fresh cut flowers or plant cuttings to a first gas mixture comprising about 80 to 98% $N_2O$, and about 2 to 20% $O_2$, with the remainder being $N_2$, under refrigeration, and
   b) subjecting said fresh cut flowers or plant cuttings to air at a temperature in the range of about 0° C. to ambient temperature.

13. The process of claim 12, wherein said refrigeration comprises a temperature of about 0° C. to 5° C.

14. The process of claim 12, which further comprises providing a continuous flow of the required gaseous mixtures through an opening in a gas tight container.

15. The process of claim 14, which further comprises adding lime to said gas tight container in an amount effective for absorbing at least a portion of $CO_2$ produced by said flowers or plant cuttings.

16. The process of claim 14, which further comprises adding lime to said oxygen permeable container in an amount effective for absorbing at least a portion of $CO_2$ produced by said flowers or plant cuttings.

17. The process of claim 12, which further comprises providing a flow of the required gaseous mixtures through an oxygen permeable material of an oxygen permeable container.

18. A process for preserving fresh cut flowers or plant cuttings, which comprises:
   a) placing said fresh cut flowers or plant cuttings in a pouch made of a barrier material and flushing the pouch with a gas mixture which is 80% $N_2O$ and 20% $O_2$,
   b) subjecting said fresh cut flower or plant cuttings to air at a temperature in the range of about 0° to ambient temperature,
   c) placing a package containing an amount of lime, effective for absorbing at least a portion of $CO_2$ produced by said cut flowers or plant cuttings in said pouch containing said cut flowers or plant cuttings, said package being made with a $CO_2$ permeability such that the $CO_2$ produced from the respiration of the cut flowers or plant cuttings will be, at least in part, absorbed by said lime; and
   b) placing said pouch containing said cut flowers or plant cuttings and lime bags in a refrigerated storage room, and storing said pouch in said storage room.

19. A process for preserving fresh cut flowers or plant cuttings, which comprises:
   a) placing said fresh cut flowers or plant cuttings in a pouch made of a barrier material and flushing the pouch with a gas mixture which is 80% $N_2O$ and 20% $O_2$,
   b) subjecting said fresh cut flower or plant cuttings to a gas mixture having about 50 to 80% $N_2O$, and having a minimum of 20% $O_2$, with the remainder being $N_2$, at a temperature in the range of about 0° to 8° C.;

c) placing a package containing an amount of lime, effective for absorbing at least a portion of $CO_2$ produced by said cut flowers or plant cuttings in said pouch containing said cut flowers or plant cuttings, said package being made with a $CO_2$ permeability such that the $CO_2$ produced from the respiration of the cut flowers or plant cuttings will be, at least in part, absorbed by said lime; and d) placing said pouch containing said cut flowers or plant cuttings and lime bags in a refrigerated storage room, and storing said pouch in said storage room.

* * * * *